United States Patent [19]

Parab

[11] Patent Number: 5,527,802
[45] Date of Patent: Jun. 18, 1996

[54] NEW USES OF 3-TETRAZOLO -5,6,7,8-SUBSTITUTED-PYRIDO (1,2-A) PYRIMIDIN-4-ONES

[75] Inventor: Prakash Parab, Williamsville, N.Y.

[73] Assignee: Bristol-Myers Squibb Company, New York, N.Y.

[21] Appl. No.: 158,081

[22] Filed: Nov. 24, 1993

Related U.S. Application Data

[63] Continuation of Ser. No. 955,532, Oct. 1, 1992, abandoned.

[51] Int. Cl.$^6$ .......................... A61K 31/505; A61K 31/14
[52] U.S. Cl. ......................... 514/258; 514/643; 514/975
[58] Field of Search ..................................... 514/258, 643

[56] References Cited

U.S. PATENT DOCUMENTS

| | | | |
|---|---|---|---|
| 3,054,678 | 9/1962 | Michener et al. | 99/150 |
| 3,472,939 | 10/1969 | Petrocci et al. | 424/329 |
| 4,122,274 | 10/1978 | Juby | 544/282 |
| 4,457,932 | 7/1984 | Juby et al. | 424/251 |
| 4,977,157 | 12/1990 | Yazaki et al. | 514/258 |
| 5,034,230 | 7/1991 | Morita et al. | 424/427 |
| 5,039,688 | 8/1991 | Lewis | 514/358 |

FOREIGN PATENT DOCUMENTS

| | | |
|---|---|---|
| 0316174A1 | 5/1989 | European Pat. Off. . |
| 2084872 | 4/1982 | United Kingdom . |

OTHER PUBLICATIONS

HCA Abstract 85:25348, Tishina, I. et al., 1976.

Primary Examiner—Raymond Henley, III
Assistant Examiner—M. Moezie
Attorney, Agent, or Firm—Anthony M. Santini

[57] ABSTRACT

New uses of certain substituted pyrido[1,2-a]pyrimidin-4-one anti-allergy drugs are made possible by the provision of clear, stable aqueous solutions of same. The aqueous solutions contain novel combinations of drugs and stabilizers.

13 Claims, No Drawings

NEW USES OF 3-TETRAZOLO -5,6,7,8-SUBSTITUTED-PYRIDO (1,2-A) PYRIMIDIN-4-ONES

This application is a continuation of application Ser. No. 955,532, filed Oct. 1, 1992 now abandoned.

BACKGROUND

Perimolast, i.e., optionally substituted 3(1H-tetrazol-5 -yl)-4H-pyrido[1,2-a]pyrimidin-4-one and pharmaceutically acceptable derivatives thereof have been taught for use as inhibitors of allergic reactions. U.S. Pat. No. 4,122,274 describes these compounds and their use in oral and parenteral formulations.

U.S. Pat. No. 4,457,932 teaches the use of this same family of drugs in formulations to treat peptic ulcers and a variety of other gastrointestinal disorders generally characterized by inflammation and necrosis. Oral and parenteral routes of administration are discussed.

European Patent Application Publication 316,174 (Tokyo Tanabe Co. Ltd., assignee) discloses aqueous preparations containing the potassium salt of 9-methyl-3-(1H-tetrazol-5 -yl)-4H-pyrido[1,2-a]pyrimidin-4-one (i.e., pemirolast potassium). The preparations contain 0.05 to 0.5% of the salt, 0.1 to 0.1% of dibasic potassium phosphate and 0.005 to 0.2% of monobasic potassium phosphate. They are used in nasal and ophthalmic compositions and in part for allergic dermatitis. The patent cites the induction of crystallization of pemirolast potassium by antiseptic benzalkonium chloride and a preference for the addition of antiseptic, such as potassium sorbate and sodium dehydroacetate. However, these antiseptics are not effective as micropreservatives in the pH range 7.0–9.0, that is, at the pH range at which pemirolast is most preferentially formulated.

U.S. Pat. No. 5,034,230 (Santen Pharmaceutical Co., Ltd., assignee) shows antiallergic eye drops which contain 9-methyl-3-(1H-tetrazol-5-yl)-4H-pyrido[1,2-a]pyrimidin-4-one (i.e., pemirolast) and its salts. The eye drops must contain specific pairs of buffers and generally include preservatives, such as benzalkonium chloride, and chelating agents, such as disodium ethylene diaminetetraacetic acid ($Na_2EDTA$).

THE INVENTION

It has been discovered that optically clear, stable aqueous solutions of optionally substituted 3(1H-tetrazol-5 -yl)-4H-pyrido[1,2-a]pyrimidin-4-one and their derivatives can be prepared. The solutions contain up to 2.0% drug(s) and from about 0.004 to about 0.02% of certain benzalkonium chlorides.

In a preferred embodiment, 2% of potassium salt of 9-methyl-3-(1H-tetrazol-5-yl)-4H-pyrido[1,2-a]pyrimidin-4-one (i.e., potassium pemirolast) is put into aqueous solution with 0.02% of $C_{12}$ benzalkonium chloride to yield a clear solution useful for ophthalmic, nasal or topical use. The solution is stable for up to two years when stored at room temperature.

OBJECTS OF THE INVENTION

It is one object of the invention to provide clear, well preserved stable solutions of certain derivatives of substituted pyrido[1,2-a]pyrimidine-4-ones, i.e., pemirolast.

It is another to provide compositions and methods for the treatment of allergic conditions of the eye, nose and skin.

DESCRIPTION OF THE INVENTION

Unless otherwise indicated, all percentages recited herein are weight percentages, based on total composition weight.

All publications referred to herein are hereby incorporated by reference.

The preparations and the methods are based upon novel aqueous solutions which contain:

(a) an anti-allergic amount of a compound of formula I:

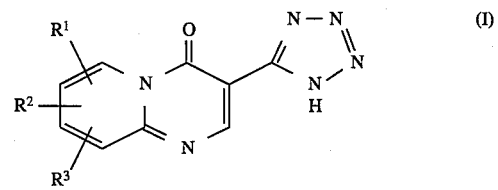

wherein $R^1$, $R^2$ and $R^3$, which may be the same or different, are each hydrogen, halogen, alkyl, cyclo alkyl, alkoxy, alkenyl, alkynyl, alkoxy, alkyl, —O—alkenyl,

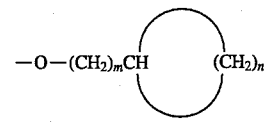

(in which m is 0 or an integer from 1 to 6 and n is an integer from 2 to 7), $—OCH_2(CH_2)_xO(CH_2)_yCH_3$, in which x and y are each independently 0 or an integer from 1 to 6, $CF_3$, hydroxy, hydroxymethyl, alkylthio, amino, nitro,

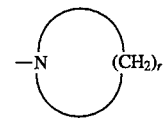

in which r is 4 or 5, alkylamino, dialkylamino, carboxyl, $—CO_2—$ alkyl, phenyl, phenyl substituted by one or two alkyl, alkoxy or halogen radicals, benzyl, alkylsulfinyl, R'—CO— in which R' is alkyl, R'—COO— in which R' is alkyl, $—O(CH_2)_kOH$ in which k is an integer from 2 to 6, or

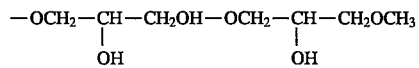

$—OCH_2C_6H_5$, or a pharmaceutically acceptable salt thereof, with the provisos that (1) when two or more of $R^1$, $R^2$ and $R^3$ are tertiary alkyl groups, they are located on non-adjacent positions and (2) no more than two of $R^1$, $R^2$ and $R^3$ may be nitro groups and all alkyl and alkenyl moieties contain from 1 to 4 C atoms.

(b) at least one mixture of $C_8$ to $C_{18}$ benzalkonium chlorides; and (c) water.

The Antiallergic Compounds

The active ingredient(s) in the systems of the invention is at least one compound of formula I above, or at least one pharmaceutically acceptable derivative thereof.

One preferred group of compounds are pemirolast, i.e., the compound of formula II,

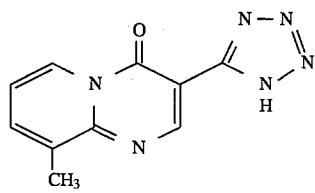

and its pharmaceutically acceptable derivatives.

By "pharmaceutically acceptable derivatives", applicant means salts, amides, esters, and the like.

Salts can be produced by contacting the appropriate hydroxides, oxides or organic amines with the acid form of the drug. Examples of pemirolast salts are metal salts, such as potassium, sodium, calcium and magnesium and organic amine salts. A highly preferred salt of pemirolast is the potassium salt.

The Benzalkonium Chloride Preservative

The phrase "benzalkonium chloride" refers to a mixture of compounds of formula III:

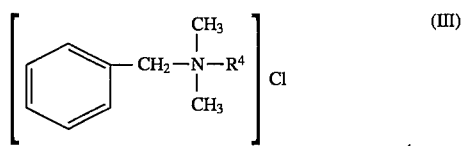

wherein $R^4$ represents a mixture of alkyl groups. $R^4$ is a normal alkyl group which contains from about 8 to about 18 carbon atoms.

In the benzalkonium chloride (BKC) mixtures, it is preferred that $R^4$ be 90% or more of a mixture of $C_8$ to $C_{12}$ homologs and most preferably be 90% or more of $C_{12}$. $C_{12}$ benzalkonium chloride alone is highly preferred.

Applicant has found that of 90% or more, and preferably more than 95%, of the $C_8$ to $C_{12}$ benzalkonium chloride fraction present in a $C_{8-18}$ mix gives remarkable clarity and stability when aqueous solutions of the drugs described herein are prepared. In fact, when a substantially pure $C_{12}$ benzalkonium chloride is used (i.e., $\leq 5\%$ of homologs other than the $C_{12}$ species are present), 2.0% of pemirolast potassium can be dissolved in the presence of about 0.004 to about 0.02% of the $C_{12}$ benzalkonium chloride to yield aqueous solutions which are stable for up to ten weeks when stored at 5° C., and a minimum of two years when stored at room temperature.

It should be noted that not all benzalkonium chlorides are operable in the invention. Those containing 10% or more of $C_{14}$ to $C_{18}$ homologs yield unstable solutions.

Water

The water used in the invention is deionized distilled water. No other treatment need be carried out.

In general, distilled water or other pharmaceutically acceptable water can be added.

pH

It is preferred that the pH of the aqueous solutions used herein be between 7.5 and 9.0, and preferably between 8.0 and 8.5. pH adjustment with such agents as potassium hydroxide and sodium hydroxide is contemplated.

Compositions

The aqueous compositions of the invention will generally contain active ingredient, benzalkonium chloride and water in the amounts given below.

| | Typical Compositions | | |
|---|---|---|---|
| Ingredient | Broad Range (%) | Preferred Range (%) | Highly Preferred Range (%) |
| A. Active Ingredient | 0.001–2 | 0.001–1 | 0.1–1 |
| B. Benzalkonium Chloride | 0.001–0.05 | 0.004–0.02 | 0.01–0.02 |
| C. pH | 7.0–9.0 | 7.8–8.7 | 8–8.7 |
| D. Excipients and Other Additives | 0–99 | 0–10 | 0–3 |
| E. Water | q.s. to 100% | q.s. to 100% | q.s. to 100% |

The compositions of the invention may include suitable amounts of one or more chelating agents such as sodium ethylenediaminetetraacetic acid (EDTA), preferably disodium EDTA, dipotassium EDTA and the like. 0.05 to 0.01 wt % of such agents are operable. Mixtures can be used.

Preferably disodium EDTA, in amounts of about 0.05 to about 0.001 wt %, and preferable about 0.01 to about 0.005 wt %, is employed.

In addition, buffers, such as mono- or dipotassium phosphate, can be added. Monobasic potassium phosphate buffer is preferred. In such embodiments, the concentration of monobasic potassium phosphate is between about 0.002 and about 0.3 wt %, with about 0.009 to about 0.045 wt % preferred. Similarly, the concentration of dibasic potassium phosphate is between about 0.1 and about 2 wt %, with 0.392 to about 1.2 wt % preferred.

In some preferred embodiments, monobasic and dibasic sodium phosphates are employed together. In those embodiments, the concentration of monobasic sodium phosphate is between about 0.002 and about 1.0 wt % with about 0.005 to about 0.02 wt % preferred; and the concentration of dibasic sodium phosphate is between about 0 1 and about 2.0% wt %, with 0.39 to about 0.6 wt % preferred. In such double buffered systems, the pH will generally lie between about 7.0 and about 9.0, with pH's of about 8.0 to about 8.7 preferred.

In addition to buffers, the compositions and methods of the invention may advantageously include chelating agents.

Other useful additives include tonicity agents, solvents, perfumes, humectants, preservatives, surfactants, colorants, viscosity modifiers and the like.

It is contemplated that active ingredients other than those of formula I and their derivatives be used. If present, additional active ingredients should constitute no more than 5 wt % of the compositions.

While ophthalmic, nasal and paintable skin formulations are described herein, it should be noted that other types of topical delivery systems are contemplated. Thus, creams, gels, ointments, powders and sprayable formulations are also operable.

EXAMPLES

The following examples illustrate the invention. In all cases, the concentration levels of the buffering agents was as specified in the tables. 0.1 to 2% of potassium pemirolast was used.

The typical method used to prepare the formulation of this invention is illustrated in Example I.

Example I

| | |
|---|---|
| Potassium pemirolast | 2.00 g |
| Potassium dihydrogen phosphate | 0.009 g |
| Dipotassium hydrogen phosphate | 0.392 g |
| $C_{12}$ BKC | 0.01 g |
| $Na_2$ EDTA | 0.01 g |
| Glycerin | 1.80 g |
| Deionized distilled water | q.s. |
| Total | 100 ml |

Preparation method:
1. The beakers, pipettes and magnetic stirrers used in the preparation of solution were washed with deionized distilled water.
2. Potassium dihydrogen phosphate and dipotassium hydrogen phosphate were dissolved in 90 ml of deionized distilled water.
3. $C_{12}$ BKC, $Na_2$EDTA and glycerin were then added to the solution and mixed to dissolve.
4. Potassium pemirolast was finally added to the solution and was dissolved by mixing for a minimum of 30 minutes.
5. The volume of the solution was then adjusted to 100 ml with deionized distilled water.
6. The solution was then filtered by passing through Millex GB 0.22 micron filter. The solution was stored in the previously washed and sterilized scintillation vials. Scintillation vials were free of dust and fibers.

In reading the tables, note that BKC means benzalkonium chloride, "NC" indicates no change, i.e., the solution was stable. The presence of (*) indicates that pemirolast crystals formed.

TABLE I

MONOBASIC SODIUM PHOSPHATE (0.008%) AND DIBASIC SODIUM PHOSPHATE (0.32%) BUFFER, pH 8.0

| Sample | Ia | Ib | Ic | Id | Ie |
|---|---|---|---|---|---|
| % $C_{18}$ BKC | 0.01 | — | — | — | — |
| % $C_{14}$ BKC | — | 0.01 | — | — | — |
| % $C_{12}$ BKC | — | — | 0.01 | — | — |
| % $C_8$ BKC | — | — | — | 0.01 | — |
| % BKC USP | — | — | — | — | 0.01 |
| % Potassium pemirolast | 0.1 | 0.1 | 0.1 | 0.1 | 0.1 |
| Stability | | | | | |
| 1 day, 5° C. | * | * | NC | NC | * |
| 4 weeks, 5° C. | * | * | NC | NC | * |
| 10 weeks, 5° C. | * | * | NC | NC | * |
| 1 day, RT (25° C.) | * | * | NC | NC | * |
| 10 month, RT (25° C.) | * | * | NC | NC | * |

BKC = benzalkonium chloride
* = crystals

TABLE II

MONOBASIC POTASSIUM PHOSPHATE/DIBASIC POTASSIUM PHOSPHATE +0.01% $c_{12}$ BKC, pH 8.0

| Potassium Phosphate Buffer | 0.023M | 0.023M | 0.023M | 0.023M | 0.023M | 0.046M | 0.046M | 0.069M |
|---|---|---|---|---|---|---|---|---|
| % $NA_2$EDTA | 0.01 | 0.01 | 0.01 | 0.025 | 0.025 | 0.025 | 0.025 | 0.05 |
| % Potassium Pemirolast | 0.5 | 1.0 | 2.0 | 0.5 | 1.0 | 0.5 | 1.0 | 1.0 |
| Stability: | | | | | | | | |
| 1 week, 5° C. | NC | NC | NC | NC | * | NC | NC | NC |
| 2 weeks, 5° C. | NC | NC | NC | NC | * | NC | NC | NC |
| 4 weeks, 5° C. | NC | NC | NC | NC | * | NC | NC | NC |
| 5 weeks, 5° C. | NC | NC | NC | NC | * | NC | NC | NC |
| 6 weeks, 5° C. | NC | NC | NC | NC | * | NC | NC | NC |
| 7 weeks, 5° C. | NC | NC | NC | NC | * | NC | NC | NC |
| 8 weeks, 5° C. | NC | NC | NC | NC | * | NC | NC | NC |
| 18 months RT (25° C.) | NC | NC | NC | NC | * | NC | NC | NC |

TABLE III

BORIC ACID 1.8%/ETHANOL AMINE 0.6% BUFFER (pH 8.66)

| Sample | IIIa | IIIb | IIIc | IIId | IIIe | IIIf |
|---|---|---|---|---|---|---|
| % $C_{12}$/BKC | .005 | .005 | .005 | 0.01 | 0.01 | 0.01 |

TABLE III-continued

BORIC ACID 1.8%/ETHANOL AMINE 0.6% BUFFER
(pH 8.66)

| Sample | IIIa | IIIb | IIIc | IIId | IIIe | IIIf |
|---|---|---|---|---|---|---|
| % Potassium Pemirolast | 1.0 | 0.5 | 0.1 | 1.0 | 0.5 | 0.1 |
| Stability: | | | | | | |
| 3 days, 5° C. | NC | NC | NC | NC | NC | NC |
| 2 weeks, 5° C. | NC | NC | NC | NC | NC | NC |
| 4 weeks, 5° C. | NC | NC | NC | NC | NC | NC |
| 6 weeks, 5° C. | NC | NC | NC | NC | NC | NC |
| 8 weeks, 5° C. | NC | NC | NC | NC | NC | NC |
| 10 weeks, 5° C. | NC | NC | NC | NC | NC | NC |
| 10 months RT (25° C.) | NC | NC | NC | NC | NC | NC |

BKC = benzalkonium chloride

TABLE IV

MONOPOTASSIUM PHOSPHATE 0.6%/DISODIUM
PHOSPHATE 0.3% BUFFER (adjusted pH to 8.54 with
potassium hydroxide)

| Sample | IVa | IVb | IVc | IVd | IVe | IVf |
|---|---|---|---|---|---|---|
| % $C_{12}$/BKC | .005 | .005 | .005 | 0.01 | 0.01 | 0.01 |
| % Potassium Pemirolast | 1.0 | 0.5 | 0.1 | 1.0 | 0.5 | 0.1 |
| Stability: | | | | | | |
| 3 days, 5° C. | NC | NC | NC | NC | NC | NC |
| 2 weeks, 5° C. | NC | NC | NC | NC | NC | NC |
| 4 weeks, 5° C. | NC | NC | NC | NC | NC | NC |
| 6 weeks, 5° C. | NC | NC | NC | NC | NC | NC |
| 8 weeks, 5° C. | NC | NC | NC | * | NC | NC |
| 10 weeks, 5° C. | NC | NC | NC | * | NC | NC |
| 10 months RT (25° C.) | NC | NC | NC | NC | NC | NC |

BKC = benzalkonium chloride

TABLE V

BORIC ACID 0.81%/SODIUM BORATE 0.67% BUFFER
(contains 0.24% potassium chloride, pH 8.2)

| Sample | Va | Vb | Vc | Vd | Ve | Vf |
|---|---|---|---|---|---|---|
| % $C_{12}$/BKC | .005 | .005 | .005 | 0.01 | 0.01 | 0.01 |
| % Potassium Pemirolast | 1.0 | 0.5 | 0.1 | 1.0 | 0.5 | 0.1 |
| Stability: | | | | | | |
| 3 days, 5° C. | NC | NC | NC | NC | NC | NC |
| 2 weeks, 5° C. | NC | * | NC | * | NC | NC |
| 4 weeks, 5° C. | * | * | NC | * | * | NC |
| 6 weeks, 5° C. | * | * | NC | * | * | NC |
| 8 weeks, 5° C. | * | * | NC | * | * | NC |
| 10 weeks, 5° C. | *. | * | NC | * | * | NC |
| 10 months RT (25° C.) | NC | NC | NC | NC | NC | NC |

BKC = benzalkonium chloride

TABLE VI

MONO (0.3%) & DISODIUM PHOSPHATE (0.15%) BUFFER
(adjusted pH to 8.54 with potassium hydroxide)

| Sample | VIa | VIb | VIc | VId | VIe | VIf |
|---|---|---|---|---|---|---|
| % $C_{12}$/BKC | .005 | .005 | .005 | 0.01 | 0.01 | 0.01 |
| % Potassium Pemirolast | 1.0 | 0.5 | 0.1 | 1.0 | 0.5 | 0.1 |
| Stability: | | | | | | |
| 3 days, 5° C. | NC | NC | NC | NC | NC | NC |
| 2 weeks, 5° C. | * | * | NC | NC | NC | NC |
| 4 weeks, 5° C. | * | * | NC | * | NC | NC |
| 6 weeks, 5° C. | * | * | NC | * | NC | NC |
| 8 weeks, 5° C. | * | * | NC | * | * | NC |
| 10 weeks, 5° C. | * | * | NC | * | * | NC |
| 10 months RT (25° C.) | NC | NC | NC | NC | NC | NC |

BKC = benzalkonium chloride

Table I illustrates the stability of potassium pemirolast with different homologs of benzalkonium chloride. It is observed that $C_{14}$ and $C_{18}$ homologs of banzalkonium chloride and benzalkonium chloride USP are incompatible with potassium pemirolast, as they formed crystals or turbid solutions at room temperature and 5° C. Benzalkonium chloride USP is a mixture of $C_8$ to $C_{16}$ homologs of benzalkonium chloride. The amount of $C_{14}$ to $C_{16}$ homologs of benzalkonium is greater than 20% in benzalkonium chloride USP and, hence, causes crystallization of potassium pemirolast solution. The $C_8$ to $C_{12}$ homologs of benzalkonium chloride are compatible with potassium pemirolast. The solutions can be stored at 5° C. and room temperature for a long time without crystallization.

Table II illustrates the stability of various strengths of potassium pemirolast solution at 5° C. and room temperature in different molar strengths of monobasic-and dibasic potassium phosphate buffers containing different concentrations of $Na_2$-EDTA. It is observed that a stable solution of 0.1 to 2% potassium pemirolast can be prepared with $C_{12}$ benzalkonium chloride in potassium phosphate buffer. The incompatibility caused by $Na_2$EDTA can be overcome by using higher molar strengths of potassium phosphate buffer.

Tables III through Table VI illustrate the stability of potassium pemirolast solution containing 0,005% to 0.01% of $C_{12}$ benzalkonium chloride and a variety of buffer systems at 5° C. and room temperature.

Tables III through Table VI show that, at 0,005 to 0.01 wt % $C_{12}$ benzalkonium chloride levels, the stability of 0.1% potassium pemirolast solution in boric and sodium borate and monosodium phosphate and disodium phosphate combination buffers is at least 10 weeks at 5° C. When boric acid/ethanolamine and monopotassium/disodium phosphate combination buffers are used, the solutions are stable for at least 10 weeks and 6 to 10 weeks at 5° C., respectively. Only at low temperature (5° C.) is crystallization observed in boric acid/sodium borate, monosodium phosphate and disodium phosphate buffer. In all systems given in Tables III to VI, the potassium pemirolast solutions are stable for a minimum of 10 months at room temperature.

Reasonable variations, such as those which would occur to a skilled artisan, can be made herein without departing from the scope of the invention.

What is claimed is:

1. A clear and stable aqueous solution comprising:
   (a) from about 0.001% to about 2.0% by weight of pemirolast or a pharmaceutically acceptable salt thereof;
   (b) from about 0.001% to about 0.05% by weight of at least one benzalkonium chloride mixture containing 90% or more of $C_8$ to $C_{12}$ homologs;
   (c) from 0 to about 99% by weight of an excipient selected from the group consisting of buffers, chelating agents, tonicity agents, solvents, perfumes, humectants, preservatives, surfactants, colorants, viscosity modifiers and mixtures thereof; and (d) q.s. water;

wherein the pH of the solution is from about 7 to about 9.

2. The solution of claim 1 containing from about 0.004% to about 0.02% by weight of (b).

3. The solution of claim 3 wherein (c) is selected from the group consisting of boric acid/sodium borate buffer, a mono- and disodium phosphate buffer, a monopotassium/disodium phosphate buffer, a boric acid/ethanolamine buffer, and disodium ethylene diaminetetraacetic acid.

4. The solution of claim 2 wherein the mixture in (b) is 90% or more of $C_{12}$ benzalkonium chloride.

5. The solution of claim 4 wherein (b) is $C_{12}$ benzalkonium chloride.

6. The solution of claim 4 wherein the pH is from about 7.8 to about 8.7.

7. The solution of claim 1 wherein (a) is potassium pemirolast.

8. The solution of claim 7 wherein (b) is from about 0.004% to about 0.02% by weight and contains 90% or more of $C_{12}$ homologs.

9. The solution of claim 8 wherein (c) is from 0 to about 10% by weight of an excipient selected from the group consisting of a boric acid/sodium borate buffer, a mono- and disodium phosphate buffer, a mono- and dipotassium phosphate buffer, a monopotassium/disodium phosphate buffer, and a boric acid/ethanolamine buffer.

10. The solution of claim 9 wherein the pH of the solution is from about 7.8 to about 8.7.

11. A method for the treatment of ophthalmic allergic conditions comprising the step of contacting ocular tissue with a composition comprising the solution of claim 1.

12. A method for the treatment of allergic conditions in a nasal passage comprising the step of contacting nasal tissue with a composition comprising the solution of claim 1.

13. A method for the treatment of allergic conditions of skin comprising the step of contacting the skin with a composition comprising the solution of claim 1.

* * * * *